United States Patent [19]

Horger, Jr.

[11] 4,078,310
[45] Mar. 14, 1978

[54] METHOD OF MAKING CROWNS AND BRIDGES AND THE OCCLUSAL AND LINGUAL STAMP THEREFOR

[76] Inventor: Otto A. Horger, Jr., 11008 Forrer Ct., Sterling Heights, Mich. 48177

[21] Appl. No.: 705,626

[22] Filed: Jul. 15, 1976

[51] Int. Cl.² ............................................. A61C 5/08
[52] U.S. Cl. ............................................ 32/12; 32/70
[58] Field of Search ............................ 32/5, 2, 12, 71; 264/19, 70

[56] References Cited

U.S. PATENT DOCUMENTS

| 1,507,476 | 9/1924 | Flanigan | 32/12 |
| 3,905,106 | 9/1975 | Costa et al. | 32/2 |

Primary Examiner—Robert Peshock
Attorney, Agent, or Firm—Cullen, Settle, Sloman & Cantor

[57] ABSTRACT

In the method of making dental crowns and bridges, wherein from a bite simulating articulated master model of the patient's jaws, there has been sliced and separated a master die of the particular tooth and adjacent jaw requiring a crown or bridge, the steps of marking a contrasting finish line on and around the master die, and applying a layer of plastic sheet spacing material around said die down to the finish line. Further steps include applying a supportive plastic coping over the spacing material overlapping the finish line, and thereafter trimming said coping at the finish line and simultaneously forming a V-shaped channel around the die in registry with the finish line. Further steps include removing the spacing material and reapplying the master die and coping to the master model. Applying molten wax into the cavity of a preselected metal stamp having an occlusal or lingual anatomy approximating the optimum shape of the particular tooth creating a preformed occlusal pattern the depth of the stamp. Inverting the occlusal pattern while plastic over said coping while applying axial pressure and heat, joining said pattern to said coping, and the final step with the master die removed from the master model, of applying molten wax to all lateral surfaces of the die from the margin to the occlusal pattern contouring same to the anatomical shape of a tooth.

The occlusal stamp refers to the posterior occlusal surface of the teeth.

The lingual stamp refers to the anterior lingual surface of the teeth.

There are two separate stamps the occlusal and the lingual stamp.

The occlusal or lingual stamp includes a metal base having a preformed margin defining a cavity adapted to receive molten wax, said cavity being of a predetermined shape of an occlusal or lingual anatomy corresponding to the optimum desired natural shape and size for a particular tooth.

20 Claims, 14 Drawing Figures

METHOD OF MAKING CROWNS AND BRIDGES AND THE OCCLUSAL AND LINGUAL STAMP THEREFOR

BACKGROUND OF THE INVENTION

Heretofore, once there had been constructed a bite-simulating articulated master model of the patient's jaws, there was sliced and separated therefrom a master die of the particular tooth and an adjacent jaw requiring a crown or bridge. The dies were trimmed and finish lines marked. A plastic coping was often built up upon the simulated tooth portion of the master die and this was normally trimmed by scissors to the desired finishing line, however, the degree of accuracy was limited, making it necessary to complete the margins with wax. This procedure was time consuming, the margins were very fragile and the area where the wax and the coping joined was often detectable, lessening the quality of the restoration. One of the many popular waxing techniques was used to complete the crown or bridge combination as requested by the doctor. The completed wax pattern was then invested, burned out and cast with a suitable dental alloy in accordance with the lost wax process.

It is an object of the present invention to substitute for the old and conventional manner of forming wax patterns, a method by which molten wax is applied into the cavity of a preselectd metal stamp having an occlusal or lingual anatomy corresponding to the optimum desired natural shape for that particular tooth in order to create a preformed occlusal or lingual pattern for the depth of the stamp. The occlusal or lingual pattern while plastic and within the stamp is inverted over the coping while applying axial pressure thereto and with the application of heat adhering said pattern to the coping.

It is another object to provide an occlusal stamp having a metal base and a preformed margin defining a cavity adapted to receive the molten wax and with the cavity having a predetermined shape and occlusal or lingual anatomy corresponding to the optimum desired natural shape and size for a particular tooth.

These and other objects will be seen from the following specification and claims in conjunction with the appended drawing.

THE DRAWINGS

It will be understood that the above drawings illustrate the steps of the present method and apparatus employed and that other steps and apparatus to carry out the present method may be employed within the scope of the claims hereafter set forth.

DETAILED DESCRIPTION OF THE INVENTION

For an understanding of the present method, there is reviewed herein the steps of the old waxing technique.

1. After an impression of the patient's mouth has been completed with a suitable impression material such as rubber-based impression material for the upper and lower jaw, instructions are given to the laboratory for a master model.

2. A master model is then made using any one of a number of well known model and die systems. One of these would include a powdered mixture of stone and water which is applied into the impression for the formation of a master model of the upper and lower jaws.

Figure 1:
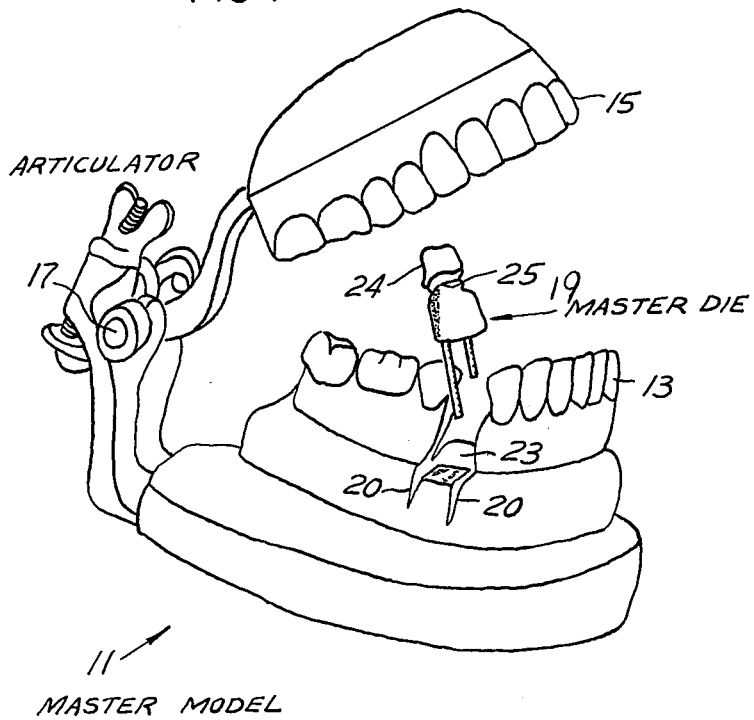
FIG. 1 is a front perspective view of an articulated master model with the jaws separated and with the master die for a particular tooth removed from the master model.

3. The master model is articulated including the opposing jaw elements to simulate the bite of the patient, such as shown in FIG. 1 of the drawing.

4. One or more removable or separate dies are cut from the master model in the majority of cases for easier fabrication of the restoration, whether it be a crown or a bridge.

5. The master die is trimmed and finish lines are marked thereon and undercut areas on the die are blocked out with a suitable "block out" material.

6. If a plastic coping has been used in the fabrication of the wax pattern for greater stability, the coping has been applied either manually or with a machine for illustration with the Erkopress, (brand name of coping systems). The plastic coping is applied to the tooth remanents in the master die upon which the crown is to be formed. With that system, the manufacturer recommended using a spray separator on the die to keep the plastic from adhering to the die. With the Erkopress system, a spacing materal of varied thickness was also recommended as applied to the die before application of the coping. The spacing material and the coping material are applied to the die at the same time.

7. Heretofore, scissors have been used to cut the coping to the desired finish line. But the degree of accuracy is limited making it necessary to complete the margins with wax. This procedure is time-consuming, the margins are very ragile and the area where the wax and the coping are joined is often detectable, lessening the quality of the restoration.

8. One of the many popular waxing techniques is used to complete the crown or bridge combination as requested by the doctor. As a final step, the completed wax pattern was then invested, i.e., surrounded by a mold material such as ceramigold investment from the Whip Mix Corporation of Louisville, Ky., or the like, the wax burned out by the application of heat and there was cast into the mold a suitable dental alloy in accordance with the lost wax process. As a final step, the restoration was cleaned, adjusted and polished.

THE NEW METHOD, i.e., THE OCCLUSAL STAMP WAXING TECHNIQUE

The present method includes the use of a metallic occlusal or lingual stamp having a base and a peripheral rim defining a cavity and with a shaft at one end secured to the base on the side thereof away from said cavity. The occlusal stamp is a metal female mold with an annular rim. In the depressed interior, thereof there is an irregular shaped cavity corresponding to the optimum desired occlusal or lingual design for a particular tooth of a particular size. The occlusal stamp can be made with or without secondary anatomy.

THE OCCLUSAL STAMP WAXING TECHNIQUE OR METHOD

The present method of making dental crowns and bridges starts with the old steps wherein from a bite-simulating master model of the patient's jaws, there has been sliced and separated therefrom a master die of the particular tooth and adjacent jaw requiring a crown or bridge;

1. Marking a contrasting finish line on and around the master die as removed from the master model using preferably a red ballpoint pen or other marker.

2. Under the Erkopress old system, a spacing material of varied thickness was recommended. In place of such manufactured spacing material, an ordinary plastic wrap, is used with superior results. Therefore, the further step includes applying a layer or two layers of plastic sheet spacing material around the die down to the finish line overlapping the same. The spacing material has a thickness of about 0.025 MM.

3. By machine or manually, a supportive plastic coping or backing is applied over the spacing material overlapping the finish line. The plastic coping has an approximate uniform thickness of about 0.60 MM, using a coping machine or a hand technique, with the coping extending usually beyond the finish line.

4. Trimming the coping at the finish line with a power-operated hand piece using an inverted cone carbide burr at the same time cutting into the master die to form a V-shaped channel around the master in registry with the finish line. Such V-shaped channel is shown at 29 FIG. 14.

Figure 2:
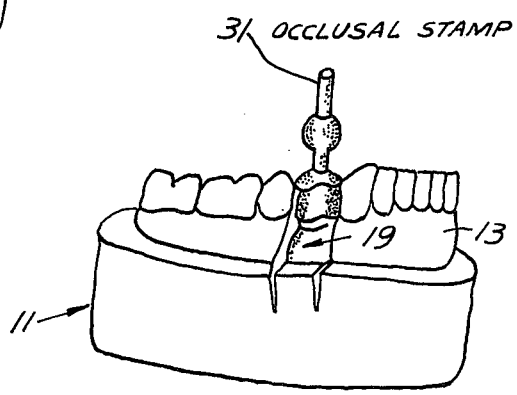
FIG. 2 is a front elevational view of a portion of the master model with the master die in place and with the occlusal stamp as it would be positioned for application of the plastic wax pattern.
Figure 3:
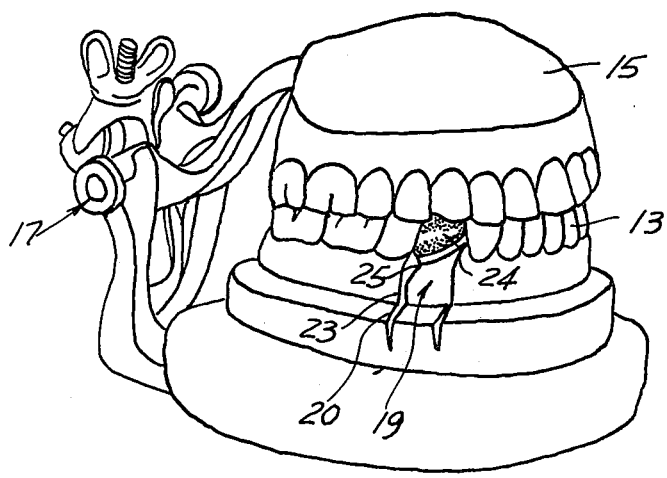
FIG. 3 is a perspective view of the master model with the jaws closed and the master die in place for checking the bite from the wax crown formation.

As shown in FIG. 1, an open master model is shown at 11 consisting of lower jaw impression 13 and upper jaw impression 15 hinged or articulated at 17. The master die 19, shown exploded in FIG. 1 from the lower jaw impression of the master model is formed by a pair of parallel cuts or slits 20 down into the master model by which the master die is separable therefrom and defining the socket 23 which removably receives said master die such as shown in FIGS. 2 and 3. As shown in FIG. 1, the tooth duplication is designated at 24 for which a crown is to be prepared or bridge.

Figure 14:
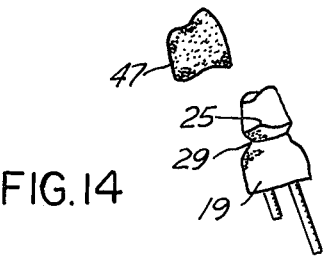
FIG. 14 is an exploded view of the completed waxed up crown ready for the investing procedure.

As heretofore mentioned, one of the initial steps was applying the finish line 25 such as shown in FIGS. 1 and 14. As a further step, the master die 19 with the coping of plastic at 27, FIG. 11 thereon is now returned to the master model such as shown in FIG. 2, but with the spacing material first removed.

Figure 8:
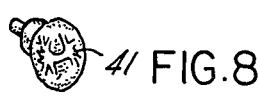
FIG. 8 is a similar view of the occlusal anatomy of an upper bicuspid.
Figure 9:
FIG. 9 is a similar view of the occlusal anatomy of an upper molar.
Figure 10:
FIG. 10 is a similar view of the occlusal anatomy of a lower molar.
Figure 11:
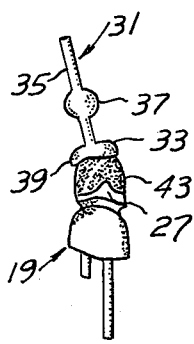
FIG. 11 is a side view illustrating the step of inverting the molten wax filled metal stamp over the coping applied to the master die.

As a further step, molten wax is applied into the cavity 41 of the metal occlusal stamp 39 shown in FIGS. 9 and 10. The occlusal stamp as shown in FIG. 11 has a metallic base 33. A shaft 35 at one end is secured to said base upon one side thereof normally extending axially thereto, though said shaft may be displaced from the central axis from said base if desired. Said base has formed upon its opposite side the peripheral preshaped rim 39 defining with respect to said base the preformed cavity 41 shown in FIGS. 5 through 10. As illustrated in FIGS. 5 through 10, each preformed cavity which is preselected has a lingual or occlusal anatomy corresponding to the optimum desired natural shape for a particular tooth for each of the teeth of the human jaws.

Figure 4:
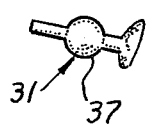
FIG. 4 is a perspective view of the lingual stamp.
Figure 5:
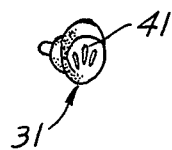
FIG. 5 is a right end view thereof showing one form of cavity, i.e., the lingual anatomy of an upper central.
Figure 6:
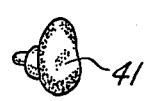
FIG. 6 is a similar view of the lingual anatomy of a lower lateral.

As part of the apparatus for utilizing the present method, there will be provided a set of the occlusal and lingual stamps of a predetermined size corresponding to the shape and contour of the natural human teeth. These have been preformed as cavities 41 such as shown illustratively in FIGS. 5 through 10. For example, FIG. 4 is a side elevational view of the present occlusal and lingual stamp approximately full scale. FIG. 5 is an end view thereof showing the lingual anatomy for an upper central. FIG. 6 is a similar view showing the lingual anatomy for a lower lateral.

Figure 7:
FIG. 7 is a similar view of the occlusal anatomy of a lower molar.

FIG. 7 is a similar view showing the occlusal anatomy for a lower molar.

FIG. 8 is a similar view showing the occlusal cavity for an upper bicuspid.

FIG. 9 is a similar view showing the cavity 41 and its surrounding rim 39 for an upper molar whereas FIG. 10 shows the cavity 41 for a lower molar.

These are illustrative of only some of the occlusal and lingual stamps employed since there should be in a set, one such stamp for each tooth. In some situations, perhaps one lingual or occlusal stamp can be applied for more than one tooth anatomy.

Each of the occlusal and lingual stamps includes upon the shaft intermediate its ends the enlargement 37 to facilitate manual application of the occlusal stamp in the steps of the present process.

Returning to the present method, a further step includes applying molten wax into the cavity of the preselected metal lingual or occlusal stamp to create a preformed lingual or occlusal pattern for the depth of the stamp. A further step includes manually inverting the stamp and the pattern therein while plastic over the coping 27 such as shown in FIG. 2 and FIG. 11. Axial pressure is applied to the stamp in the relationship shown in FIG. 2 and at the same time, heat is applied for adhering the pattern from the stamp to the coping such as shown in FIG. 11. The wax occlusal pattern is indicated at 43 as applied to the coping 27, FIGS. 11 and 12. The occlusal stamp is manipulated during the preceding step so as to apply the occlusal pattern for the correct occlusion relative to the coping 27 such as shown in FIG. 11.

As an intermediate step, before the step of forming the occlusal pattern, a separating agent is applied to the surface areas of the master model which defines the cavity 23, FIG. 1. Many companies supply separating agents or die lubricants, such as the J. M. May Company in Bloomfield, Con., and the J. F. Jalenko Company in New Rochelle, N. Y.

A further step includes after the proper selection of the occlusal stamp, a separating agent being applied to the occlusal stamp and the excess agent blotted with a paper towel.

The molten wax that is appled into the metal stamp creates a preformed occlusal pattern 43, FIG. 11, for the depth of the stamp and as defined by the shape of the cavity and the peripheral margin or rim 39.

Figure 12:
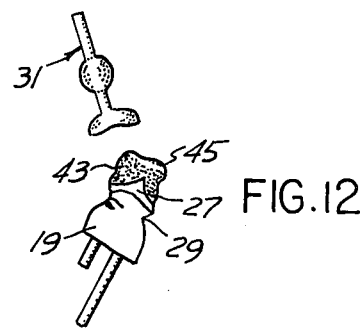
FIG. 12 illustrates a further step with the master die removed from the master model and molten wax partially applied to the lateral surfaces thereof.
Figure 13:
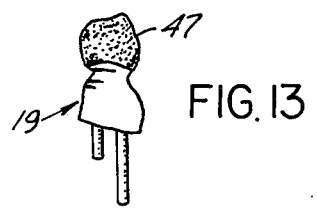
FIG. 13 illustrates the finished carved crown.

The wax pattern and the coping are joined employing a heated instrument and after cooling to a point, the metal stap is removed leaving the wax pattern 43 attached to the coping 27, such as shown in FIG. 11 and FIG. 12. As a further step, with the unit master die, coping and occlusal pattern now removed from the master model, a further step includes applying molten wax to all the lateral surfaces 45 of the master die extending from the margin or V-shaped channel 29 to the occlusal pattern 43, such as shown in FIG. 12, contouring the master die to the anatomical shape of a tooth. This is known as the bulk waxed crown. Thereafter, the wax crown is allowed to cool and is finish carved in the usual manner, such as shown at 47 assembled upon the master die 19. FIG. 14 shows the waxed up crown 47 as removed from the master die ready for the conventional investing procedure.

The present occlusal stamp waxing technique and method steps are unique in one very important way, namely, its versatility throughout the waxing procedure. As a further step in the present process, if the pattern was placed out of occlusion or the wrong stamp was used, or in checking the bite, the height of the pattern was low or high, this is followed by a simple melting step and with the possible addition of wax to the occlusal surface would then permit the technician to restamp the crown and manipulate the stamp until the best possible occlusion is obtained while still in a model. Thereafter, the wax crown is finish carved.

The present method therefore provides a very fast technique for completing the waxing of a crown.

Having described my invention, reference should now be had to the following claims:

I claim:

1. In the method of making dental crowns and bridges, wherein from a bite simulating articulated master model of the patient's jaws, there has been sliced and separated therefrom a master die of the particular tooth and adjacent jaw requiring a crown or bridge; the following steps:
   a. marking a contrasting finish line on and around the master die;
   b. applying a layer of plastic sheet spacing material around said die down to said finish line; and simultaneously
   c. applying a tooth build up plastic coping or backing over said spacing material;
   d. trimming said coping at said finish line and simultaneously forming a V-shaped channel around the master die in registry with said finish line;
   e. reapplying said master die and coping to the master model, first removing said spacing material;
   f. applying molten wax into the cavity of a preselected metal occlusal stamp, having an occlusal anatomy corresponding to the optimum desired natural shape for that particular tooth, creating a preformed occlusal pattern the depth of the stamp;
   g. inverting the occlusal pattern while plastic over said coping, while applying axial pressure thereto adhering said pattern to said coping while applying heat thereto;
   h. and with the unit die, coping and occlusal pattern removed from the master model, applying molten wax to all lateral surfaces of the die from the margin to the occlusal pattern, contouring same to the anatomical shape of a tooth.

2. In the method of maaking dental crowns and bridges of claim 1, said assembly being adapted for the final steps of investing, burning out the wax, and casting with a suitable dental alloy in accordance with the lost wax process.

3. In the method of making dental crowns and bridges of claim 1, the additional step before step (e) of applying a separating agent to the opposing areas of the master model for registry with the waxed crown.

4. In the method of making dental crowns and bridges of claim 1, said spacing material being about 0.025 MM thick.

5. In the method of making dental crowns and briges of claim 1, said coping being built up to a thickness of about 0.060 MM.

6. In the method of making dental crowns and bridges of claim 1, said metal occlusal stamp having a perhiphal margin surrounding its cavity, said stamp being selected from the group of occlusal stamp cavity shapes including lingual anatomy upper central, lingual anatomy lower lateral, occlusal anatomy lower molar, occlusal anatomy upper molar, occlusal anatomy, upper and lower bicuspid molar, and occlusal anatomy upper and lower cuspids.

7. In the method of making dental crowns and bridges of claim 1, said metal occlusal stamp having a raised peripheral margin and a base defining said cavity of predetermined anatomical shape; and
   a support shaft at one end joined to and projecting axially of said base.

8. In the method of making dental crowns and bridges of claim 7, an annular enlargement upon said shaft intermediate its ends to facilitate manipulation of said stamp for steps (g) and (h).

9. In the method of making dental crowns of claim 1, said finish lines being applied with a red ballpoint pen.

10. In the method of making dental crowns of claim 1, said spacing material being in one or two layers to achieve the maximum fit.

11. In the method of making dental crowns of claim 1, the sides of the master die defining said V-shaped channel being at an angle of about 45°.

12. In the method of making dental crowns of claim 1, after the selection of the predetermined proper occlusal stamp as to size and shape of cavity, the further step before step (f) of applying a separating agent to the cavity surfaces.

13. In the method of making dental crowns and bridges of claim 1, the further step following step (g) of cooling the die, coping and pattern and separating and removing the metal stamp, leaving the wax pattern attached to the coping.

14. In the method of making dental crowns of claim 1, the further step before step (h) of replacing the master die, coping and formed wax pattern into the articulated master model and checking the bite.

15. In the method of making dental crowns of claim 14, the further steps, when the wax pattern is placed out of occlusion, the wrong wax stamp applied, or said stamp is too high or too low, of melting the first applied wax pattern, applying the additional molten wax to the occlusal surface and restamping the crown in accordance with step (g).

16. In the method of making dental crowns of claim 15, the further step before step (h) of manipulating the metal stamp and its formed wax pattern until the best possible occlusion is obtained, with the master die still assembled in the model.

17. An occlusal or lingual stamp for use in the making of dental crowns and bridges comprising:
   a metallic base having a preformed peripheral margin defining a cavity adapted to receive molten wax when the cavity is positioned to open upwardly, said cavity being of a predetermined shape and occlusal or lingual anatomy corresponding to the optimum desired natural shape and size for a particular tooth of any human mouth, and a shaft of reduced size relative to said base at one end secured to said base and extending axially away from said cavity.

18. In the occlusal and lingual stamp of claim 17, an enlargement upon said shaft intermediate its ends to facilitate manipulation of said stamp.

19. In the occlusal and lingual stamp of claim 17, there being a set of said lingual and occlusal stamps for a particular size of tooth, with each stamp having a different cavity, corresponding respectively to the general anatomical lingual and occlusal shape of all of the teeth of both human jaws.

20. In the method of making dental crowns and bridges, wherein from a bite simulating articulated master model of the patient's jaws, there has been sliced and separated therefrom a master die of the particular tooth and adjacent jaw requiring a crown or bridge; and wherein a contrasting finish line is marked on and around the master die; a plastic coping is applied to the die, trimmed to said finish line and a V-shaped channel is formed around the master die in registry with said finish line; and said master die and coping is reapplied to the master model, the following steps:
   a. applying molten wax into the cavity of a preselected metal stamp, having a lingual or occlusal anatomy corresponding to the optimum desired natural shape for that particular tooth, creating a preformed occlusal pattern the depth of the stamp;
   b. inverting the occlusal pattern while plastic over said coping, while applying axial pressure thereto adhering aid pattern to said coping while applying heat thereto;
   c. and with the unit die, coping and occlusal pattern removed from the master model, applying molten wax to all lateral surfaces of the die from the margin to the occlusal pattern, contouring same to the antomical shape of a tooth.

* * * * *